(12) United States Patent
Weed et al.

(10) Patent No.: US 9,510,766 B2
(45) Date of Patent: Dec. 6, 2016

(54) INSERTABLE PROBE

(71) Applicant: Mississippi State University Research And Technology Corporation (RTC), Mississippi State, MS (US)

(72) Inventors: Benjamin C. Weed, Starkville, MS (US); Ali Borazjani, Starkville, MS (US); Jun Liao, Starkville, MS (US)

(73) Assignee: Mississippi State University (MSU), Starkville, MS (US)

( * ) Notice: Subject to any disclaimer, the term of this patent is extended or adjusted under 35 U.S.C. 154(b) by 186 days.

(21) Appl. No.: 14/209,316

(22) Filed: Mar. 13, 2014

(65) Prior Publication Data

US 2014/0275841 A1    Sep. 18, 2014

Related U.S. Application Data

(60) Provisional application No. 61/780,198, filed on Mar. 13, 2013.

(51) Int. Cl.
*A61B 5/00* (2006.01)
*A61B 5/0488* (2006.01)

(52) U.S. Cl.
CPC ....... *A61B 5/04882* (2013.01); *A61B 5/04884* (2013.01); *A61B 5/4337* (2013.01)

(58) Field of Classification Search
CPC .......... A61B 5/04882; A61B 5/04884; A61B 5/4337
USPC .................. 600/300, 301, 546, 587, 591
See application file for complete search history.

(56) References Cited

U.S. PATENT DOCUMENTS

| | | | | |
|---|---|---|---|---|
| 5,167,237 A | * | 12/1992 | Rabin | A61B 5/205 128/836 |
| 5,515,853 A | * | 5/1996 | Smith | A61B 5/0422 128/916 |
| 5,779,638 A | * | 7/1998 | Vesely | A61B 5/0422 600/437 |
| 6,063,045 A | * | 5/2000 | Wax | A61M 25/10 482/112 |
| 7,079,882 B1 | * | 7/2006 | Schmidt | A61B 5/4041 600/373 |
| 2004/0030360 A1 | * | 2/2004 | Eini | A61B 5/04882 607/39 |
| 2005/0065408 A1 | * | 3/2005 | Benderev | A61B 5/208 600/202 |

(Continued)

*Primary Examiner* — William Thomson
*Assistant Examiner* — John R Downey
(74) *Attorney, Agent, or Firm* — Butler Snow LLP (57) ABSTRACT

A device and method for measuring the structural integrity and structural health of the female pelvic floor, or other lumenal organ, is disclosed. Said device comprises an insertable probe with a pressure chamber capable of distending the walls of said lumenal organ. The invention also comprises means for positioning the pressure chamber and adjusting its location along the lumen. Said device also comprises means for changing and recording the volume and pressure of a balloon which is part of the pressure chamber, and means for determining and recording the location of the walls of the balloon. Said device also comprises a means for integrating information obtained to determine important biomechanical information, such as stress-strain curves, which a medical clinician can use for diagnostic purposes. Said method comprises the insertion of said probe, the expansion and contraction of the pressure chamber under desired condition, and means for analyzing obtained data for increased usefulness to the clinician.

9 Claims, 10 Drawing Sheets

(56) References Cited

U.S. PATENT DOCUMENTS

| | | | |
|---|---|---|---|
| 2005/0124920 A1* | 6/2005 | Gregersen | A61B 5/053 600/593 |
| 2006/0004286 A1* | 1/2006 | Chang | A61B 5/06 600/435 |
| 2008/0077053 A1* | 3/2008 | Epstein | A61B 5/0053 600/591 |
| 2008/0183105 A1* | 7/2008 | Greenhalgh | A61B 5/1076 600/587 |
| 2009/0030288 A1* | 1/2009 | Abboud | A61B 5/053 600/300 |
| 2010/0030113 A1* | 2/2010 | Morriss | A61B 1/233 600/585 |
| 2012/0064537 A1* | 3/2012 | Ross | C12N 5/0068 435/6.13 |
| 2012/0109012 A1* | 5/2012 | Cinbis | A61B 5/1076 600/587 |
| 2013/0218050 A1* | 8/2013 | Eichhorn | B82Y 15/00 600/587 |

\* cited by examiner

INSERTABLE PROBE

CROSS-REFERENCES TO RELATED APPLICATIONS

This application claims the benefit of and priority to U.S. provisional application Ser. No. 61/780,198 filed on Mar. 13, 2013, which is incorporated herein by reference in its entirety.

FIELD OF THE INVENTION

The field of the invention is the diagnostics and measuring of properties of interior spaces such as lumens of bodies, for example, in the gynecological and intestinal systems.

BACKGROUND OF THE INVENTION

Pelvic Organ Prolapse (POP) and other associated pelvic floor disorders are among the fastest growing health concerns worldwide. POP affects 50% of all women who have given birth, and is the $2^{nd}$ leading indication for surgery among women. Total US societal costs for treating and managing POP are over $29 Billion.

POP is characterized by the loss of structural integrity of the supporting tissues (muscles, ligaments, tendons, etc.) within the female pelvis. As the support tissues weaken, pelvic organs (vagina, bladder, rectum, and bowel) begin to protrude in to the vaginal canal and towards the vaginal opening. This leads to numerous complications including urinary and fecal incontinence, pain and ulcerations, sexual discomfort, and many psycho-social complications.

The most common cause of POP is childbirth. As the baby's head passes through the vaginal canal, the pelvic tissues undergo extreme stretch, pressure, and other potentially injurious conditions. This can lead to different injury mechanisms including, but not limited to: obstetric laceration for tearing of tissues or nerves, nerve fiber crushing, obstruction of blood flow to vaginal tissues leading to temporary ischemia, and levator muscle trauma. The risk of these injuries is increased by many factors such as obesity, previous injury, small maternal anatomy, large fetal weight and/or head size, and the presence of underlying connective tissue disorders. These injuries may be severe enough to cause POP symptoms shortly after childbirth. The more common scenario occurs as a progressive degenerative process. Muscle and nerve injuries sustained during childbirth may take years to reach a symptomatic level. In particular atrophic weakening of muscles due to nerve damage, combined with a decrease in hormonal tissue maintenance associated with the onset of menopause, leads to a relatively abrupt shift from asymptomatic POP to highly symptomatic POP when surgical interventions are likely. This age-related scenario is why 11% of all women will require a surgery to correct their POP by age 65. Factors that increase risk for POP later in life include obesity, heavy-lifting, endurance or high-impact athletics, and other conditions which may greatly or repeatedly increase the patient's intra-abdominal pressure.

The underlying phenomenon of the POP pathology, the process that leads to symptomatic POP, and the surgical treatments that correct POP are all inherently mechanical or structural. The ability to evaluate the structure of the organs and tissues involved in POP is crucial to understanding, diagnosing, and treating this pathology. The most common diagnostic method for evaluating POP is a physical exam of the pelvis conducted by a physician or nurse along with the completion of a brief "scoring" system (the Pelvic Organ Prolapse Quantification system or POPQ) which stages the prolapse as grade 1-4. This system is quick and effective, but inherently subjective. Other diagnostic techniques include urodynamics testing, which involves filling and draining of the urinary bladder while measuring certain diagnostic parameters. Vaginal manometry is another common technique, in which a balloon is inserted into the vagina and inflated while pressure is tracked. A similar technique to vaginal manometry is employed to evaluate the structural competency of the anus and rectum, called anorectal manometry (ARM). These techniques all seek to evaluate the way lumenal tissues respond to specific loading conditions. These existing systems are limited by their ability to simultaneously track the magnitude of the load and the magnitude of the displacement of the structures they evaluate.

Current in vivo biomechanics methods limit the ability of researchers, and greatly limit the potential for application of biomechanics in day-to-day diagnostics/treatment for practicing clinicians. What is needed is a tool allowing researchers and physicians to perform in vivo biomechanics studies of the vagina or rectum (or any other lumenal tissues, as is relevant) in a manner that does not require an expensive, separate medical imaging system, and which produces objective data.

SUMMARY OF THE INVENTION

The present invention eliminates the above difficulties and disadvantages by providing an insertable probe for measuring the properties of a lumen. According to one aspect of the invention, the insertable probe comprises a pressure chamber secured to a first end of a shaft, a second end of the shaft being controlled by a user, a system for inflating and deflating the pressure chamber, a system for measuring deformation of the pressure chamber as it inflates and deflates, and a system for measuring the internal pressure of the pressure chamber, such that when the user moves the pressure chamber along the axis of the lumen and the pressure chamber is inflated or deflated, data on the properties of the lumen can be collected.

According to another advantageous feature of the invention, the insertable probe may further comprise a pressure chamber shaft and a balloon having two ends, each end being secured tightly to opposite ends of the pressure chamber. Also, the pressure chamber shaft of the insertable probe may be split.

According to another advantageous feature of the invention, the insertable probe may further comprise the end of the pressure chamber opposite the user being secured to or forming an insertable tip.

According to another advantageous feature of the invention, the system for inflating and deflating the pressure chamber may further comprise a pump connected by tubing to the interior of the pressure chamber. Also, the pump may be a syringe pump. Furthermore, the pump may be used in pumping a substantially noncompressible fluid.

According to another advantageous feature of the invention, the system for measuring the deformation of the pressure chamber as it inflates and deflates may further comprise a sonomicrometry system.

According to another advantageous feature of the invention, the system for measuring the deformation of the pressure chamber as it inflates or deflates may further comprise at least two electronically charged crystals being affixed to the balloon communicating with each other, and sending data to a processor.

According to another advantageous feature of the invention, the system for measuring the internal pressure of the pressure chamber may be a pressure catheter connected by a pressure catheter cable to a processor.

According to another advantageous feature of the invention, the insertable probe may further comprise a system for measuring muscle activity of the walls of the lumen, including EMG sensors affixed to the exterior of the pressure chamber, said EMG sensors connected to a processor.

According to another advantageous feature of the invention, the system for measuring the deformation of the pressure chamber as it inflates and deflates may further comprise a sonomicrometry system.

According to another aspect of the invention, the insertable probe for measuring the properties of a lumen comprises a shaft connected to a source of torque, a pressure chamber which is propelled by the source of torque in either direction along the shaft, a system for inflating and deflating the pressure chamber, a system for measuring deformation of the pressure chamber as it inflates and deflates, and a system for measuring the internal pressure of the pressure chamber, such that when the pressure chamber moves along the axis of the lumen and the pressure chamber is inflated and deflated, data on the properties of the lumen can be collected.

According to another advantageous feature of the invention, the insertable probe may further comprise a pressure chamber shaft and a balloon having two ends, each end being secured tightly to opposite ends of the pressure chamber.

According to another advantageous feature of the invention, the insertable probe may further comprise the pressure chamber being propelled along the shaft in either direction by a source of torque engaged mechanically by any one of a number of means selected from the group consisting of a lead screw and nut, a chain and sprocket in a loop, a track and sprocket or gear, a translating shaft plus sliding shaft, and a cable and spool.

According to another advantageous feature of the invention, the insertable probe may further comprise the shaft being a lead screw threaded through a nut affixed to the pressure chamber, so that when the lead screw turns the pressure chamber moves in either direction through the shaft hole in the central slider. Also, the insertable probe may further comprise at least one stabilizer rod connected to the insertion tip and an anchor in the enclosure.

According to another advantageous feature of the invention, the insertable probe may further comprise an insertable tip being attached to the end of the shaft opposite the source of torque.

According to another advantageous feature of the invention, the system for inflating and deflating the pressure chamber may further comprise a pump connected by tubing to the interior of the pressure chamber. Also, the pump may be a syringe pump. Furthermore, the pump may be used in pumping a substantially noncompressible fluid.

According to another advantageous feature of the invention, the system for measuring the deformation of the pressure chamber as it inflates and deflates may further comprise at least two electronically charged crystals being affixed to the balloon, communicating with each other and sending the data to a processor.

According to another advantageous feature of the invention, the system for measuring the internal pressure of the pressure chamber may be a pressure catheter connected by a pressure catheter cable to a processor.

According to another advantageous feature of the invention, the insertable probe may further comprise a system for measuring muscle activity of the walls of the lumen, including EMG sensors affixed to the exterior of the pressure chamber, said EMG sensors connected to a processor.

BRIEF DESCRIPTION OF THE DRAWINGS

Further advantages of the invention will become apparent by reference to the detailed description of preferred embodiments when considered in conjunction with the drawings which form a portion of the disclosure and wherein:

FIGS. 7A and 7B show features in an embodiment without a motor and a central slider.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The invention is an insertable probe containing a pressure chamber 1 containing the means, as described herein, to measure the properties of a lumenal structure such as, for example, the vaginal canal, the rectum or anal sphincter.

The insertable probe is comprised of an insertion tip 2 capable of easy insertion into the appropriate lumenal structure. In one embodiment for assessing the female pelvic floor the insertion tip 2 is designed to insert easily and comfortably into the vagina without encouraging dilation of the cervix. The insertion tip 2 is accomplished, in one embodiment, with a piece having 2 rounded steps, cut so that the first step is narrow enough to easily separate the labia as would be the case with a cone, but is blunt enough to prevent cervical dilation as would be the case with a cone. In another embodiment, the anatomical tip can be cast, molded or formed in one piece.

The pressure chamber 1 moves down the lumen and obtains data from inside the lumen. The pressure chamber 1 can be self-propelled inside the lumen by different means, without changing the character of the invention. For instance, the pressure chamber 1 can be self-propelled by a source of torque such as a motor by, without limitation, a lead screw and nut; a chain and sprocket in a loop; a track and sprocket or gear; a translating shaft plus sliding shaft; and cable and spool.

In one embodiment, the insertion tip 2 is connected, by a freely rotating joint, to a shaft 4, having a first end 4*a* and a second end 4*b*, which is a lead screw. The lead screw is connected with a coupling to a drive shaft which is connected, through gears and couplings, to a motor which provides a source of torque. The motor drives the lead screw. The lead screw is connected to a lead screw-driven nut which connects to a pressure chamber 1. This combination conducts the pressure chamber 1 back and forth along the length of the lead screw.

When inflated, the pressure chamber 1 distends the tissues being measured in a particular location within the lumen. The insertion tip 2 is rounded to provide for easy entry into the lumen and, in one embodiment, it is affixed to first and second stabilizer rods 5, 6. The stabilizer rods 5, 6 provide a sliding track for the central slider 10, and also prevent the slider from spinning in place in the lead screw embodiment when the lead screw turns, i.e., some measure of force must be applied to break the static friction with the lead screw and beginning moving along the screw. As for the embodiments using motorized propulsion (self-propulsion), the central slider 10 needs a track along which it travels. The stabilizer rod (5 or 6) is a very simple and easy example of that but, alternatively, any track and slider system could be used.

Alternatively, there is an embodiment with only one stabilizer rod 5 such as a motor system with a tube around a lead screw, which is substantially a stabilizing agent. The insertion tip 2 does not rotate because the shaft 4, in one embodiment rotating as a lead screw, ends at the insertion tip 2 but is not affixed to it, as there is a bearing in the insertion tip 2 to allow the lead screw to rotate without moving the insertion tip 2. The shaft 4 and the stabilizer rods 5, 6 extend from the insertion tip 2 to the enclosure 26 of the device where, in one embodiment, the source of torque, such as an electric motor, is located. The stabilizer rods 5, 6, in one embodiment, fit into female slots on the insertion tip 2 and an anchor component within the enclosure 26. They are further secured within these slots by any mechanical means such as cup point set screws.

The insertion tip 2 is at the patient end of the device, and the enclosure 26 end with the motor or the hand grip for the physician is at the user end. There are two protective sleeves 13 to protect the patient from moving parts, preferably composed of a durable polymer, which cover the shaft 4 and stabilizer rods 5, 6, one being connected to the insertion tip 2 and a sleeve attachment 7 at the patient end of the slider, and the other being connected to a sleeve attachment 7 at the user end of the slider and also to the device housing at the user end. Each sleeve attachment 7 is connected to the slider caps 12, 17. The sleeves 13 are merely for protection from moving parts and are not inflated.

Figure 8:
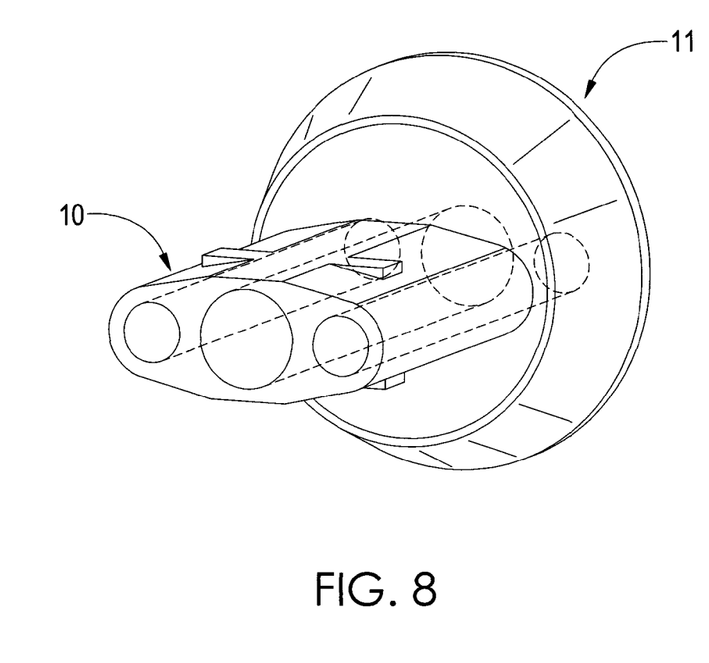
FIG. 8 is a perspective view of a cross-section of the central slider in the embodiment with a motor and a lead screw.

In one embodiment, the pressure chamber 1 comprises a balloon 3, a central slider 10, slider ends 11, 16, slider caps 12, 17, a system for inflating the balloon 3, a system for tracking the deformation of the balloon 3, and a system for capturing fluid pressure in the interior 27 of the pressure chamber 1. In this embodiment, each end of the balloon 3 is secured tightly between a slider end and slider cap. FIG. 8 shows a cross-section of the central slider 10 and slider end 11 in an embodiment with a motor and a lead screw. Pressure chamber 1 is secured a first end 4*a* of shaft 4. A second end 4*b* of shaft 4 is then free to be controlled by a user.

A system for inflating the balloon 3, in one embodiment, includes a pump for moving fluid into and out of the balloon 3 by means of a tube 15 secured by a tube fitting 14 in which the flow is both controlled and monitored. In one embodiment, a syringe pump is employed in which the flow of 4-5 mL/s is achieved, and in which the flow is monitored by the position of the syringe plunger. Preferably, a substantially noncompressable fluid is used in the system, as is well known in the art. In another embodiment a flow meter is employed. The pump controls the flow of any substantially non-compressible liquid, such as water or silicone oil, into the pressure chamber 1.

Figure 1:
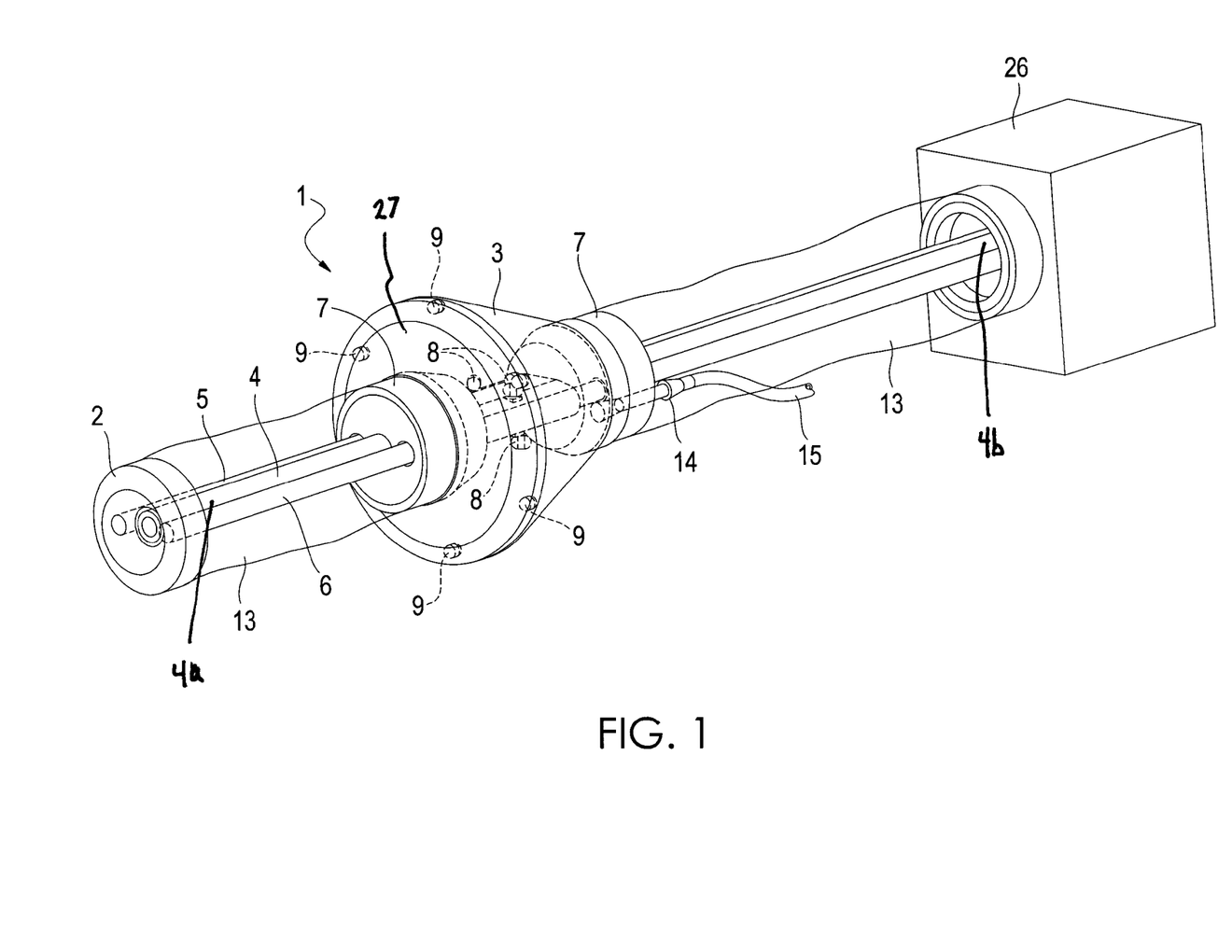
FIG. 1 is a perspective view from the patient side of the invention in the embodiment with a motor and lead screw.
Figure 2:
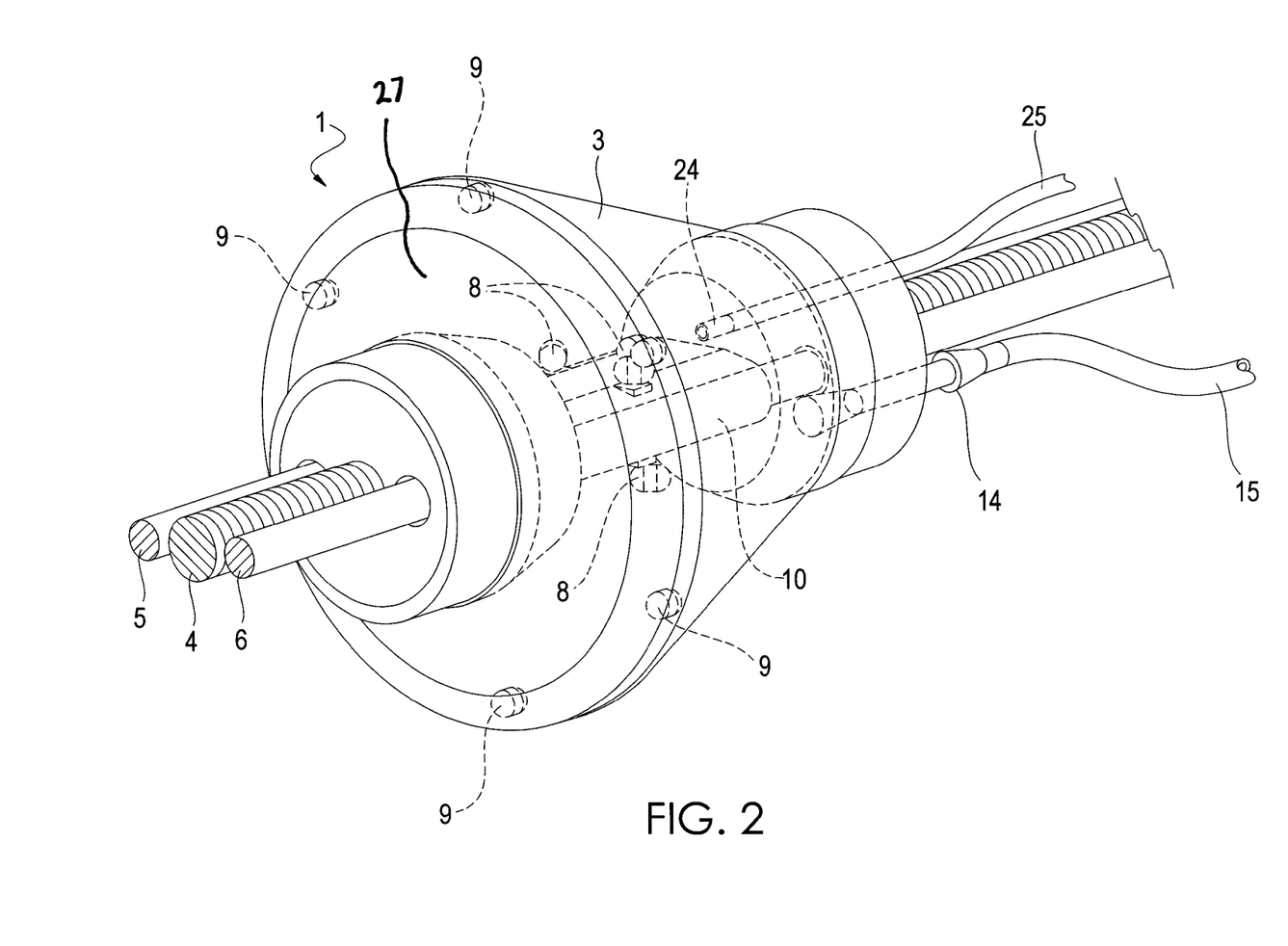
FIG. 2 is closer perspective view of the pressure chamber (containing the central slider, balloon, slider ends, slider caps, reference crystals and floating crystals) in the embodiment with a motor and lead screw.
Figure 7A:
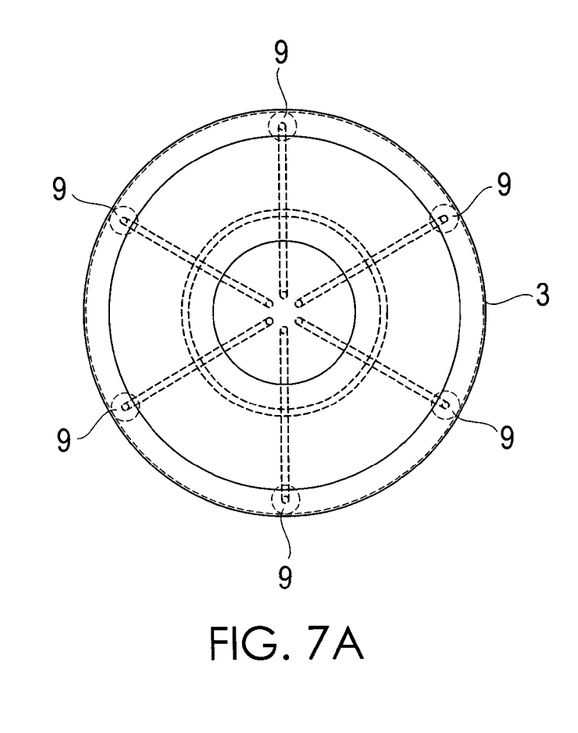
FIG. 7A is a cross-section of the balloon showing an embodiment with 6 floating crystals affixed to the interior surface of the balloon, and with wires attached to the floating crystals.
Figure 7B:
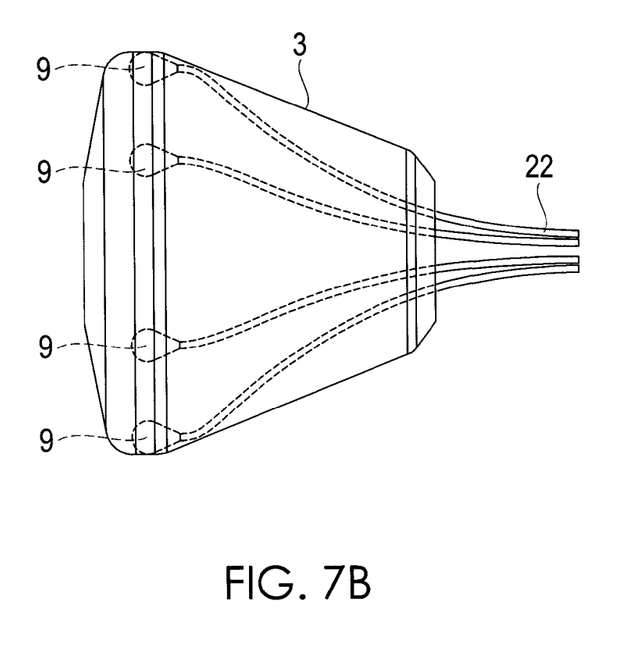
FIG. 7B is a side view of the balloon showing the floating crystals and wires in dotted and solid lines.

The system for tracking the deformation of the lumen is, in one embodiment, a sonomicrometry system such as found, for example, in U.S. Pat. Nos. 5,515,853, and 5,779,638, which are herein incorporated by reference. A sonomicrometry system, in one embodiment, consists of reference crystals 8 affixed to a central slider 10 and floating crystals 9 affixed in a ring-like pattern to the interior surface of the balloon 3, preferably at the largest circumference of the balloon 3 while inflated. When sonomicrometry is employed, in one embodiment, there are at least 2 reference crystals 8 on each side of the central slider 10, which communicate ultrasonically with at least 1 floating crystal 9 affixed to the interior surface of the balloon 3. In another embodiment (as in FIGS. 1 and 2) there are 3 reference crystals 8 affixed to each side of the central slider 10, for a total of 6 reference crystals 8, and 3 floating crystals 9 on the interior surface of the balloon 3 on each side of the central slider 10, for a total of 6 floating crystals 9. The number of reference crystals 8 and floating crystals 9 may vary, depending on the amount of data sought or the nature of the lumen being probed. In an embodiment of the crystals where they are elongated and electric wires are attached at one end called a tail from which ultrasound is not emitted, the crystals are positioned so that the tails do not point at each other. Each of the floating crystals 9 and reference crystals 8 transmits data to a processor by means of a wire 22 for each (as shown in FIGS. 7A & 7B), said wires 22 leading through a port 23 in the user end of the pressure chamber 1, and the wires 22 are directed out to a unit which processes the data.

In one embodiment, all crystals act as transmitters and receivers. If all crystals are collecting data, this creates the most robust data set. The reference crystal 8 is a fixed location from which to make projections about other crystals (knowns or boundary values in the system of equations). In an embodiment with 3 reference crystals 8 affixed to the central slider 10, the minimum would be, for example, a floating crystal 9 making a pulse which is read by the reference crystals 8 to create a tetrahedron in 3D space. The optimum configuration is for each crystal to communicate with each other to have the most robust data set; the 3 reference crystals 8 would still function as knowns in the system of equations.

The embodiment with a pressure chamber shaft which is a split shaft 21 and fewer crystals eliminates complex 3D and focuses on the landmark distances. For this reason the anterior/posterior crystals function as an A to B distance and the left/right crystals serve as a C to D distance. In this embodiment there is no known anchor point because the device does not solve for geometry but graphs the distances versus pressure and obtains a diameter value. In the latter embodiment, the device also calculates values like aspect ratio change with a vertical/horizontal value.

Figure 3:
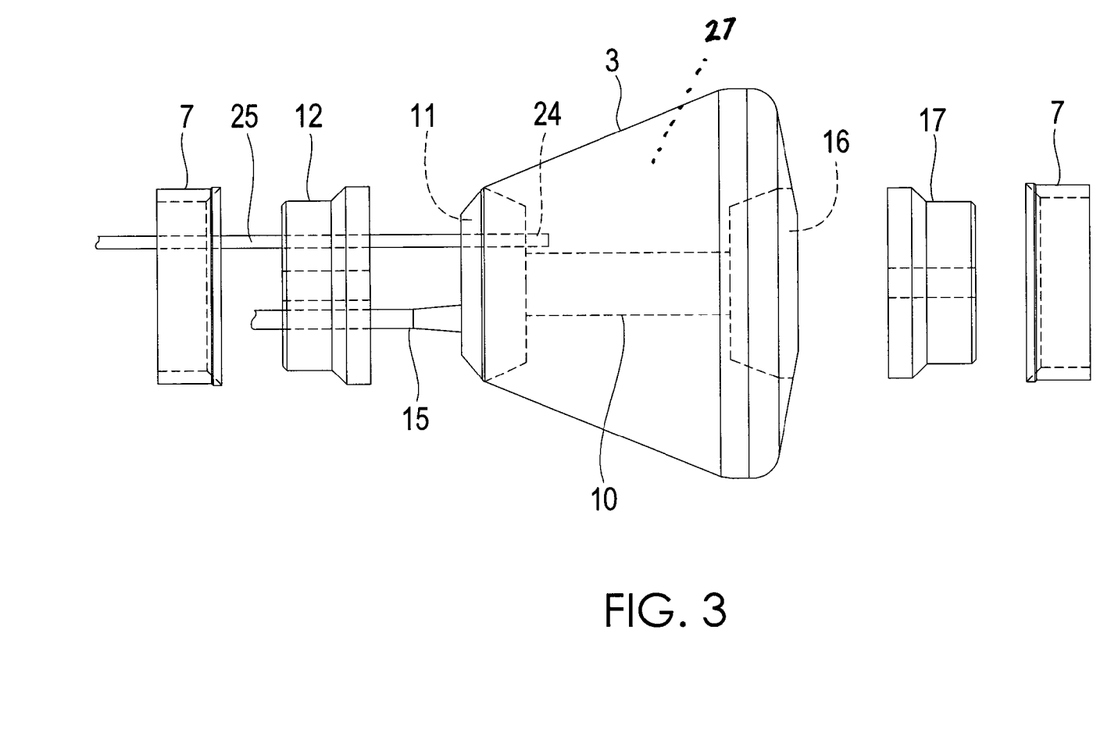
FIG. 3 is an exploded view of the pressure chamber from the side including the balloon, central slider and slider ends, slider caps, and a portion of the oil tube in the embodiment with a motor and lead screw.
Figure 4:
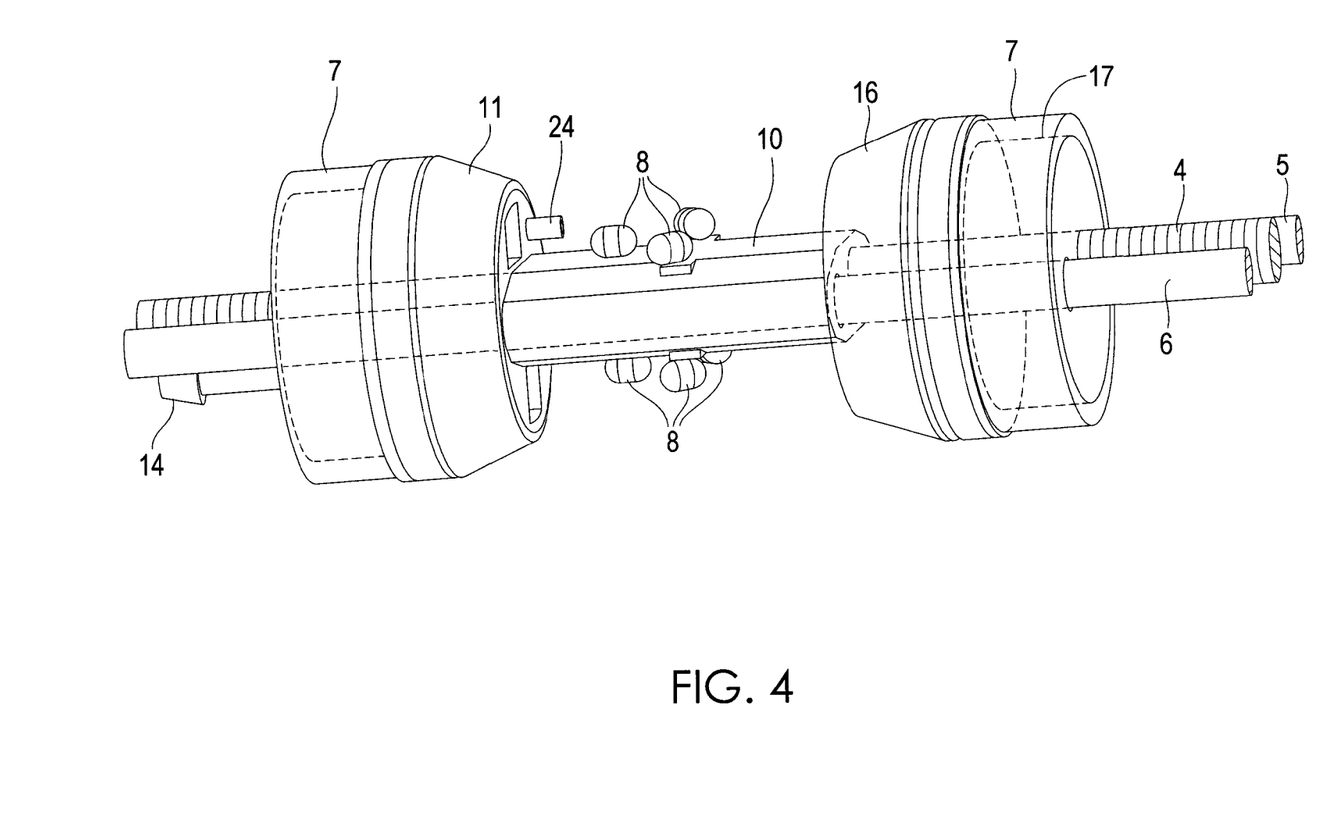
FIG. 4 is detail, in the embodiment with a motor and lead screw, of the pressure chamber without the balloon, showing the reference crystals attached to the central slider, the slider ends, the slider caps, and the shaft and a stabilizer rod.

The system for measuring the internal pressure of the pressure chamber 1, in one embodiment, in the embodiment in FIGS. 3 and 4, includes a pressure catheter cable 25 connected to a pressure catheter 24, typically at the end of a pressure catheter cable 25, which measures the fluid pressure of the environment it occupies, for example, a Millar brand Mikro-Tip Pressure Catheter. The pressure catheter 24 may be inserted into the pressure chamber 1 through a port 23, or through a separate hole, in the user slider end 11 and user slider cap 12, and measures the pressure of the fluid inside the balloon 3. The sensing part of the catheter is within the pressure chamber 1 and not directly in the way of the fill/drain port to the syringe pump, as this could create a local increase in pressure due to flow.

Figure 5:
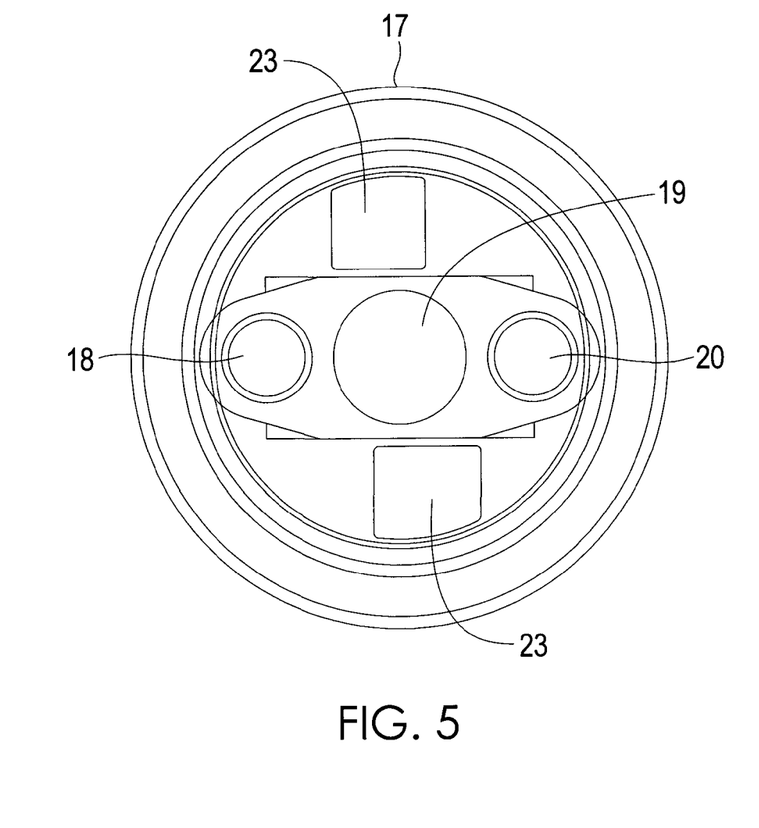
FIG. 5 is the user slider end.

There is at least one port 23 in the user end 11 of the central slider 10 to conduct all the components (tube 15, wires 22, and pressure catheter cable 25) present in the system. In one embodiment there is a tube fitting 14 for securing the tube 15 as it enters the pressure chamber 1. The pressure chamber 1, in an embodiment with the lead screw, further comprises a threaded nut which fits snugly against the lead screw, allowing the lead screw to turn and, by so doing, moves the pressure chamber 1 in either direction. The nut can be a separate piece affixed to the pressure chamber 1, or can be a threaded surface on any of the openings through which the lead screw passes, for example, the patient slider cap 17. As can be appreciated in FIG. 5, there is a shaft hole 19 through which the shaft 4 extends, and the shaft hole 19 can be threaded for interface with the shaft 4 in the embodiment with a lead screw. There are also first and second stabilizer rod holes 18, 20 for each stabilizer rod 5, 6 when these rods 5, 6 are provided.

Another method for propelling the pressure chamber 1 is a chain and sprocket in a loop. In this embodiment the shaft 4 runs from the enclosure 26 to the insertion tip 2, through the central slider 10. The shaft 4 allows the central slider 10 to slide freely along its length. The method of conducting the central slider 10 along the shaft 4 is a rotating shaft in the insertion tip 2, and a rotating shaft in the enclosure 26. There are 2 rotating shafts connected together by a means of transmitting power from one shaft to the other, such as a chain and 2 sprockets, or a belt and 2 pulleys. The chain is also connected to the central slider 10, so that when the chain moves, the central slider 10 moves with the chain. One of the rotating shafts is also connected to a motor which turns the rotating shaft to conduct the chain and the central slider 10 forward or backward along the shaft 4.

Another method for propelling the pressure chamber 1 is a track and sprocket or gear. In this embodiment the central slider 10 moves along the shaft 4, which runs from the enclosure 26 to the insertion tip 2 through the central slider 10. There is also a track such as a chain, belt, or a toothed track, which also may be an additional feature of the shaft 4 or a separate feature. There is an appropriate means for interfacing with this track such as a sprocket, pulley, or gear, which is attached to a rotating shaft on the slider. The rotating shaft on the central slider 10 is connected to a motor which turns the rotating shaft to conduct the central slider 10 forward and backward along the shaft 4 and track assembly.

Another method for propelling the pressure chamber 1 is a translating shaft plus a sliding shaft. In this embodiment the central slider 10 moves along a stabilizing shaft, which runs from the insertion tip 2 through the central slider 10. There is also a second translating shaft which is firmly connected to the user end of the central slider 10 without passing all the way through to the insertion tip 2. The translating shaft is also connected to a linear positioner, such as a non-captive style motor and lead screw assembly (non-captive motors sold, for example, by Haydon Kerk Motors) or a piezo positioner assembly (see RodDrive Ultrasonic Motor Actuator at Physyike Instruments Piezo Positioners) within the enclosure 26. The linear positioner can then move the translating shaft forward or backward to conduct the central slider 10 along the length of the sliding shaft.

Another method for powering the pressure chamber 1 is a cable and spool with a stabilizing shaft along which the central slider 10 moves freely. There is a cable, belt, or chain firmly attached to the user end of the central slider 10, similarly to the embodiment involving a translating shaft, above. The cable, belt or chain engages a spool, pulley or sprocket within the enclosure 26. The spool is attached to a rotating shaft, which is attached to a motor, which rotates in one direction to move the central slider 10 from the tip towards the enclosure 26. Because this embodiment uses a means of conducting the slider that is only effective in tension, the central slider 10 must be manually moved in the direction of the tip. There is another embodiment with a cable and spool with a sufficiently small cable/spool/shaft/motor assembly on the tip and connected to the patient slider end 16. In this embodiment the 2 motors tug against one another to propel the central slider 10 in either direction.

In one embodiment the balloon 3 in the pressure chamber 1, which covers a portion of the longitudinal axis of the shaft 4, is configured so that when fully inflated the largest circumference of the balloon 3 can be in the middle of the balloon 3 or at any other points including the ends. When the largest circumference is at the patient end of the balloon 3, as in FIGS. 1 and 2, the invention can record data nearest the end of the lumen. In other embodiments, the balloon 3 is constructed so that more than one point on its length has the largest circumference when inflated.

In one embodiment the tracking of the balloon 3 is achieved using a stereophotometry system which uses multiple cameras and markers to determine 3-dimensional geometry. Additionally, electromyographic (EMG) sensors can be placed at desired locations on the interior or exterior of the balloon 3 or central slider 10 to measure muscle activity or contractions alone or in combination with other acquired data. This combination allows the physician to simultaneously see the load between the balloon 3 and the tissues, the amount of displacement caused by these loads, the total change in volume of the balloon 3, and the relative strength of the muscle contractions which may or may not be currently contributing to these loads.

The central slider 10 may be comprised of any suitable material such as stainless steel, aluminum or plastic sufficient to support the balloon 3 which applies load to the tissues. In one embodiment the balloon 3 is a durable polyurethane polymer of medical grade. When the balloon 3 is not inflated it collapses. The positions of the floating crystals 9 as the balloon 3 inflates or deflates provide data on the size and shape of the lumen. In another embodiment, the same functionality could also be achieved with stereophotometry or any other three-dimensional tracking system.

The shaft 4 stabilizes the relatively dynamic length and shape of a lumen such as the vagina. The shaft 4 also serves to accurately position, in one embodiment, through motor driven rotation, the pressure chamber 1 within the vagina or other lumen. Additionally, the ability to position accurately within the vagina is important for testing specific regions of interest such as the area just below the bladder neck.

Figure 6:
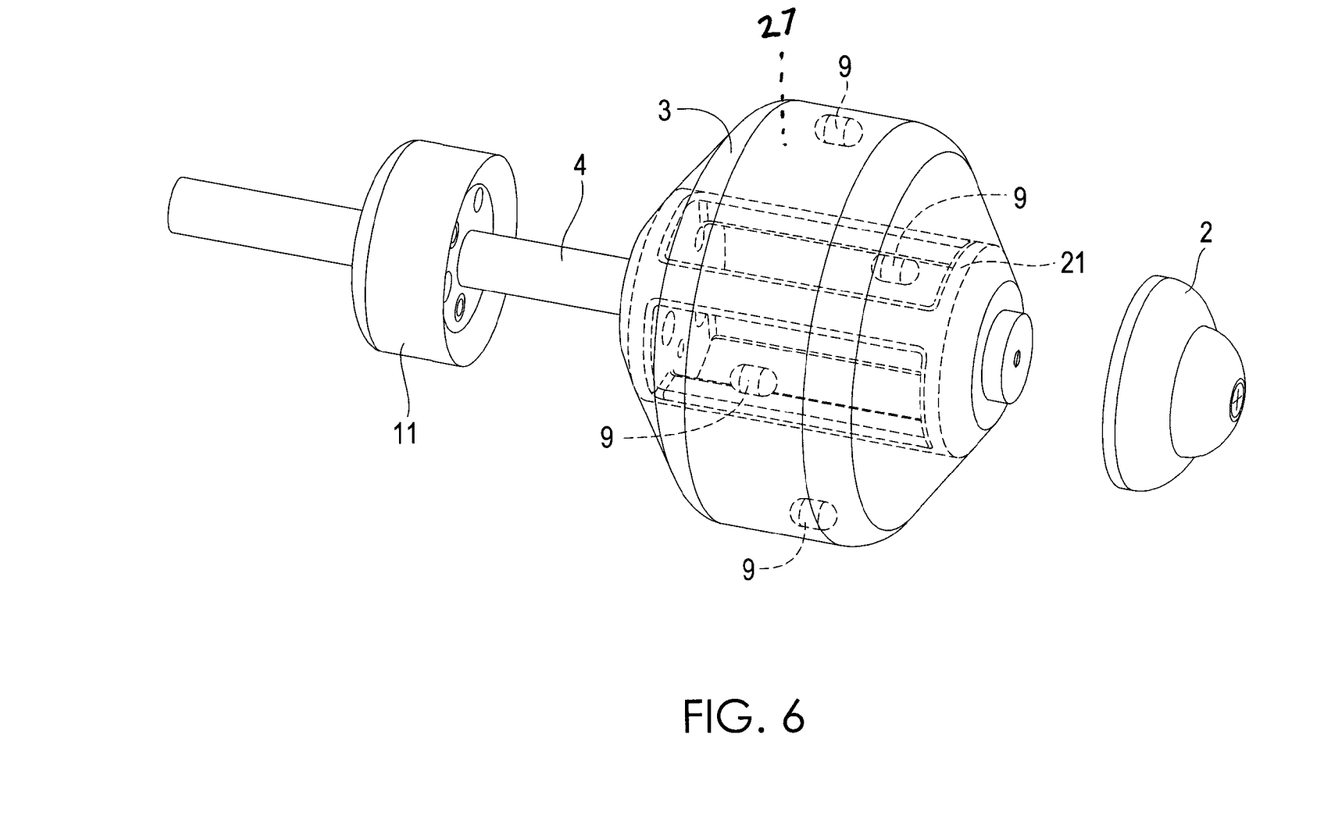
FIG. 6 is a perspective view of the invention in the embodiment with a pressure chamber shaft which is a split shaft, in an embodiment without a motor and a central slider.

In another embodiment the pressure chamber 1 comprises a pressure chamber shaft which is a split shaft 21, as depicted in FIG. 6, which allows a line of sight between the floating crystals 9, thus requiring no reference crystals 8 as when the invention employs the central slider 10. In the embodiment with the split shaft 21 there are at least 2 floating crystals 9. Four floating crystals 9 are depicted in the embodiment in FIG. 6. The split shaft 21 is most commonly used in an embodiment in which the pressure chamber 1 is not self-propelled. The user end of the pressure chamber 1 with the split shaft 21 is affixed to the end of the shaft 4 and the patient end of the pressure chamber 1 is adjacent to the insertion tip 2. If stabilizer rods 5, 6 are used with the embodiment with the split shaft 21, the stabilizer rods 5, 6 terminate at the user end of the pressure chamber 1. Thus, there is no shaft or stabilizer rod blocking the line of sight between the floating crystals 9, and the split shaft 21 eliminates the need for reference crystals 8, as the floating crystals 9 act as their own references for each other. In this embodiment there is neither a motor nor a central slider 10 and the pressure chamber 1 is mounted next to the insertion tip 2, and the physicians moves the pressure chamber 1 in or out manually. In the embodiment without a motor, the pressure chamber 1 can be attached to any component which allows insertion and control of the pressure chamber 1, such as flexible member or robotic arm, instead of a rigid shaft.

The power usage of the electric motor in driving the lead screw (or other means of self-propulsion) is related to the torque required in movement of the pressure chamber 1 in or out of the lumen. Analysis of the power usage thus provides additional information about the structural characteristics of the lumen, particularly the frictional forces the lumen places on an object moving within the lumen. In one embodiment the torque applied by the motor is measured using a torque cell.

The invention is a unique solution to capture load and displacement and other measurements such as stiffness, bulk modulus, vaginal surface area, vaginal volume, vaginal friction, elasticity, extensibility, ductility, and Finite Element Analysis (FEA) integration. Compliance, stiffness, bulk modulus, and elasticity are all quantities related to the tissues ability to resist deformation under load. Vaginal surface area and volume are indications of the relative size of the vagina, as well as the way that size changes under loading. Vaginal extensibility and ductility are measures of a tissues ability to accommodate deformation, extensibility indicating accommodation of deformation without significant load, and ductility indicating accommodation of deformation without significant damage. FEA simulations based on this data allow prediction of many potentially deleterious situations for the lumen. This includes simulations of the likely outcomes of potential surgical treatments, or vaginal childbirth. The simulation is used as an assistive tool in selecting a particular mesh versus non-mesh POP reconstruction, or as a risk assessment tool to identify women at high risk for severe obstetric trauma or difficulty.

Other devices have sought to obtain data on in vivo vaginal biomechanics through expensive and cumbersome combinations of loading systems and various medical imaging modalities, but the present invention achieves the objective without those. The issues associated include cost, availability of imaging hardware, as well as the fact that some of the methods for assessing in vivo vaginal biomechanics are only suitable to a specific animal (rat) and cannot be directly translated into other animals (sheep or human).

There is also provided a computer controlled system for (1) managing testing procedures including a pressure catheter 24, pump, motor, propulsion system, and sensors; (2) acquisition, management and analysis of data acquired during testing protocols; and (3) visualizing the data graphically. For obtaining data, the system conducts the tests described above according to appropriate user inputs. This process includes scripting capability for loading and unloading based on pressure, volume, displacement of crystals, or other mechanical parameter; pausing for stress relaxation; positioning for specific locations or for profiling. It also includes pre-scripted processes for the vaginal biomechanics profile, load-unload mechanical testing, stress-relaxation, cough/contraction, and other routines encountered in the testing. For processing the system takes the data and processes it according to user inputs or pre-programmed defaults, at the user's option. This includes conversion of straight-line sonoextensometry data to 3D Cartesian coordinates via a Euclidean-distance-based algorithm and preparation of the corresponding data files for output and analysis. For visualization the system outputs visual information for the user to interpret. In the simple load/unload test this includes stress-versus-strain plots for both pressure and displacement related terms including circumference, surface area, volume, specific directions.

By means of the invention, vaginal biomechanics data may be obtained as described herein including, without limitation, a 2-dimensional data plot of the sensors on the balloon 3, a stress versus strain plot for desired testing protocols and selected parameters, a vaginal biomechanics profile (VBP) and other desired data visualization criteria.

Additionally, a mechanism is provided for positioning and holding the insertable probe during testing/diagnostics. In one embodiment this is a locking-arm system attached to a medical table already possessing stirrups. This mechanism, either comprising or connected to the enclosure 26, allows for positioning the insertable probe into the vagina, for example, to a comfortable depth, while the patient is in supine position with legs in stirrups. The locking-arm system will then be locked in place to prevent motion during usage.

The invention allows for the tracking of load and deformation in real time, and thus can be used to create stress-versus-strain curves which describe material behavior under mechanical loading. This general technology has specific applications in the following applications, as well as others:

1. The device is inserted into the patient to a desired depth, such as the depth of the cervix when the vagina is relaxed and the patient is in supine position with legs in stirrups.

2. The pressure chamber is moved to a desired location, such as directly below the bladder.

3. The balloon 3 is inflated to a desired volume or pressure value, and at a desired speed, then stops when the pressure or volume threshold is reached.

4. The balloon 3 is held at the above reached volume for a desired amount of time. This may be from zero seconds, up to as much as an hour if stress relaxation behavior is of interest. Alternatively, the balloon 3 may quickly be inflated to a desired pressure, then continually inflated at a very slow inflation rate in order to maintain the desired pressure. This technique would allow the observation of creep phenomenon. This alternative method must be used carefully to avoid injury.

5. The balloon 3 is then deflated to the original volume.

6. Data (load, marker location, time, volume, etc.) from this testing method is then used to create load-versus-displacement curves, or other derivatives thereof, such as stress-versus-strain curves, and load-versus-time curves.

7. This data may be further processed to identify specific parameters (i.e. stiffness, extensibility, bulk modulus, novel parameter(s) identified from the described device's data set) of interest to the researcher or clinician.

Figure 9A:
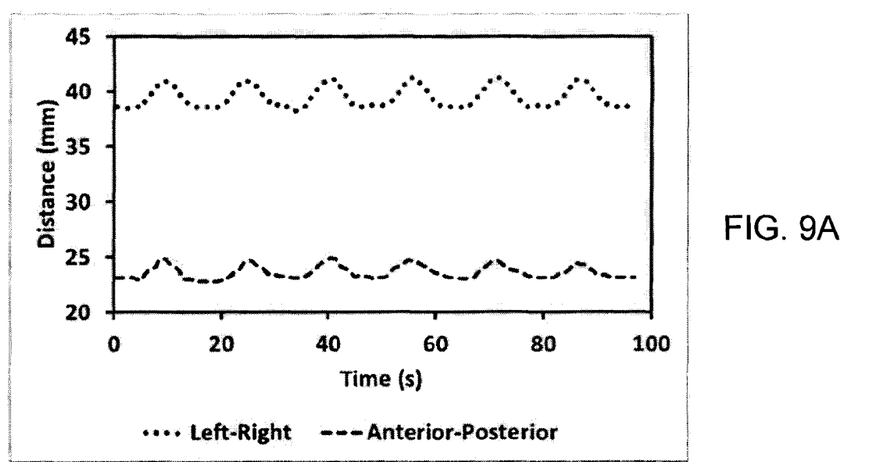
FIGS. 9A and 9B show data generated from an embodiment while inserted in a patient. Specifically, the charts show data of changing distance (FIG. 9A) and pressure (FIG. 9B) data are plotted vs. time to indicate the progression of the testing process.
Figure 9B:
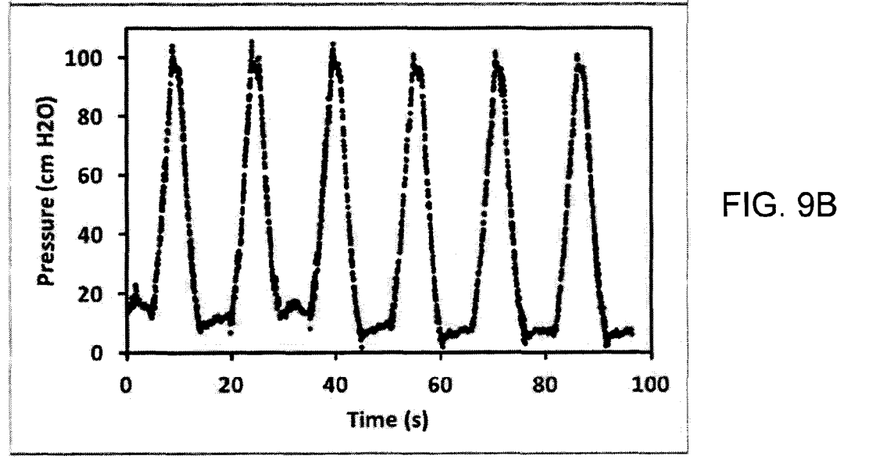

8. FIGS. 9A & 9B indicates an example of the above mentioned type of data where changing distance and pressure data are plotted vs. time to indicate the progression of the testing process.

Figure 10:
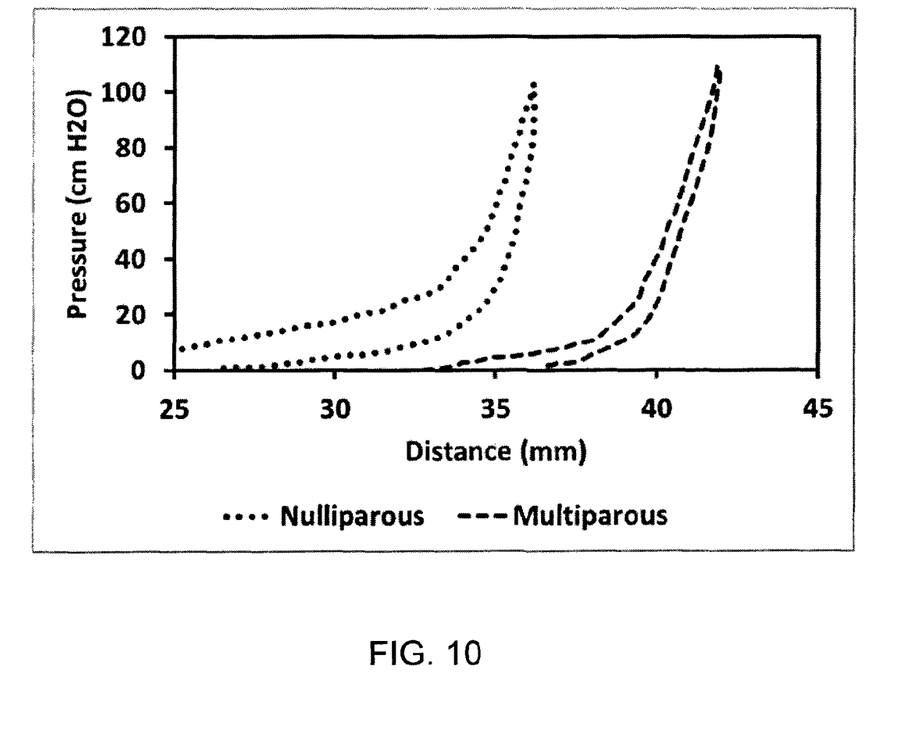
FIG. 10 shows data generated from an embodiment while inserted in a patient, where pressure is plotted vs. changing distance to indicate load vs. displacement relationship.

9. FIG. 10 indicates an example of the above mentioned type of data, where pressure is plotted vs. changing distance to indicate load vs. displacement relationship.

To obtain a VBP:

1. Deflate the pressure chamber 1, move it to the tip of the device, and insert the device to the cervix 2. Inflate the pressure chamber to a specified pressure, typically of low to moderate load; well below any discomfort threshold.

3. Without changing the volume within the pressure chamber 1, the pressure chamber is conducted away from the cervix at constant velocity until it completely exits the vagina. The device collects data comprising sonomicrometry data, intra-chamber pressure, and torque, at regular increments of pressure chamber displacement.

4. The device is then deflated and retracted from the patient.

5. Data obtained from the profiling test can be displayed to highlight the changes in response to load along the vaginal canal.

a. Consider a 3-dimensional Cartesian coordinate system in which the z-axis is parallel to the length of the vaginal canal, the y-axis extending towards patient's anterior vaginal wall, and the x-axis extends towards the patient's left vaginal wall. The origin of this coordinate system is designated as the center of the shaft 4 at the z-axis location of the ring of crystals when the device and pressure chamber are positioned at the cervix.

b. The straight-line data obtained by the sonomicrometers is converted into (xcrystal, ycrystal, zcrystal) data via a Euclidean distance-based system of equations. This (xcrystal, ycrystal, zcrystal) data represents the location of the floating crystals 9 relative to the reference crystals 8 and creates a ring of floating crystals 9 for a given pressure chamber location along the profile (0,0,zchamber).

c. Rings of floating crystal 9 coordinates are then plotted in (x, y, z) space as (X, Y, Z)=(xcrystal, ycrystal, zcrystal)+ (0,0,zchamber). (X, Y, Z) is now the location of the crystals at their location relative to the beginning of the test.

d. A plot of all the rings creates a wireframe model for the final display of the vaginal biomechanics profile. The wireframe model is then filled in with color-shaded polygons which correspond to a color-contour table for intra-chamber pressure.

e. The resulting mesh allows for the rendering of a 3D display of pressure versus displacement along the length of the vagina. This structural snapshot can capture subtle changes in the vaginal environment, which is of potential interest to researchers and clinicians concerned with pelvic floor disorders.

The above described techniques and procedures may be used in a number of diagnostic, preventative and therapeutic modes including, without limitation, the following:

1. Diagnosis/characterization of lumenal strength and structural integrity. This information is directly related to the presence and severity of structural disorders of, for example, the pelvic soft tissues such as pelvic organ prolapse or other pelvic floor disorders.

2. Creation of a "baseline" parameter, similar to a patient's normal blood pressure, which is related to lumenal health. This allows the continuous tracking of a patient's progress allowing for personalized medicine.

3. Diagnosis/identification of patients at high risk for obstetric or other trauma or complications. Structural data is used to evaluate the vagina's ability to accommodate the loading during childbirth, so the clinician can make more informed decisions regarding interventions (C-section, forceps, vacuum suction, for example)

4. Evaluation of surgical interventions which seek to restore structural integrity to the female pelvic floor. These surgeries employ meshes, slings, and major repair and restructure of tissues. Assessment of the structural effects of these procedures allows for better tracking of progress and better understanding of patient's benefits/complications associated with the surgery.

5. The evaluation of therapy progress, as in physical therapy or fitness training. These therapies seek to strengthen the vaginal tissues through commonly used methods.

6. Detection or characterization of obstetric fistulas or locations which have been compromised in a manner which may eventually become an obstetric fistula.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. An insertable probe for measuring the properties of a lumen, comprising:
   a. a pressure chamber secured to a first end of a shaft, a second end of the shaft configured for being controlled by a user,
   b. a pressure chamber shaft within the pressure chamber, the pressure chamber shaft being split to form one or more openings,
   c. two or more diametrically-opposed sonomicrometry crystals affixed to the pressure chamber, wherein the two or more diametrically-opposed sonomicrometry crystals are arranged in a manner allowing direct line of sight between the two or more diametrically-opposed sonomicrometry crystals to pass through the one or more openings of the pressure chamber shaft,
   d. a system for inflating and deflating the pressure chamber,
   e. a system for measuring deformation of the pressure, wherein the system for measuring deformation of the pressure chamber is comprised of the two or more diametrically-opposed sonomicrometry crystals that are electronically charged and in communication with each other and a processor for receiving data from the two or more diametrically-opposed sonomicrometry crystals, and
   f. a system for measuring the internal pressure of the pressure chamber, such that when the pressure chamber is moved along the axis of the lumen and the pressure chamber is inflated or deflated, data on the properties of the lumen can be collected.

2. The insertable probe as in claim 1, the pressure chamber further comprising:
   g. a balloon having two ends, each end being secured to opposite ends of the pressure chamber.

3. The insertable probe as in claim 1, further comprising the end of the pressure chamber opposite the second end of the shaft being secured to or forming an insertable tip.

4. The insertable probe as in claim 1, in which the system for inflating and deflating the pressure chamber further comprises a pump connected by tubing to the interior of the pressure chamber.

5. The insertable probe as in claim 4, further comprising the pump being a syringe pump.

6. The insertable probe as in claim 4, further comprising the pump capable of pumping a fluid.

7. The insertable probe as in claim 1, in which the system for measuring the internal pressure of the pressure chamber is a pressure catheter connected by a pressure catheter cable to the processor.

8. The insertable probe as in claim 1, further comprising a system for measuring muscle activity of the walls of the lumen, including EMG sensors affixed to the exterior of the pressure chamber, said EMG sensors connected to the processor.

9. The insertable proper of claim 1, where the shaft is flexible.

\* \* \* \* \*